(12) United States Patent
Gordon et al.

(10) Patent No.: US 10,420,543 B2
(45) Date of Patent: Sep. 24, 2019

(54) SCAPHO-LUNATE AND OTHER LIGAMENT AND BONE REPAIR/RECONSTRUCTION

(71) Applicants: Leonard Gordon, Mill Valley, CA (US); Joshua A Leonard, Philadelphia, PA (US)

(72) Inventors: Leonard Gordon, Mill Valley, CA (US); Joshua A Leonard, Philadelphia, PA (US)

(*) Notice: Subject to any disclaimer, the term of this patent is extended or adjusted under 35 U.S.C. 154(b) by 424 days.

(21) Appl. No.: 13/730,930

(22) Filed: Dec. 29, 2012

(65) Prior Publication Data

US 2013/0172893 A1    Jul. 4, 2013

Related U.S. Application Data

(60) Provisional application No. 61/582,174, filed on Dec. 30, 2011.

(51) Int. Cl.
*A61F 2/42* (2006.01)
*A61B 17/04* (2006.01)
*A61B 17/16* (2006.01)
*A61B 17/17* (2006.01)

(52) U.S. Cl.
CPC ...... *A61B 17/0401* (2013.01); *A61B 17/0469* (2013.01); *A61B 17/16* (2013.01); *A61B 17/1796* (2013.01)

(58) Field of Classification Search
CPC ............ A61B 17/0466; A61B 17/0469; A61B 17/0487; A61B 2017/0409; A61B 2017/0488; A61B 2017/0445; A61B 2017/1782
See application file for complete search history.

(56) References Cited

U.S. PATENT DOCUMENTS

2009/0234396 A1*  9/2009  Medoff ................ A61F 2/4601
606/86 R

* cited by examiner

*Primary Examiner* — David Bates
*Assistant Examiner* — Samuel Hanna

(57) ABSTRACT

Methods and kits are provided to treat scapho-lunate ligament tears, which involve stabilization of the scaphoid and lunate both dorsally and volarly. The treatments can be performed through open, mini-open or arthroscopic procedures, as an intra-capsular or extra-capsular repair and stabilization procedure. The treatment procedures involve the use of sutures or wires to fix the relative orientations of the scaphoid and lunate, and the optional use of bone anchors or other bone attachment devices to create a capsulodesis between the lunate and scaphoid, or other bones, to lift the scaphoid into the desired position. Localization of the entry point of the sutures or wires into the bones are used to improve positioning of the bone anchors, sutures and wires.

8 Claims, 7 Drawing Sheets

SCAPHO-LUNATE AND OTHER LIGAMENT AND BONE REPAIR/RECONSTRUCTION

BACKGROUND

The wrist joint comprises a number of articulations between a) the radius and ulna and the carpal bones of the wrist, b) the articulations between the carpal bones themselves, and c) the articulations between the carpal bones may be characterized as having a proximal row of bones (scaphoid, lunate, triquetrum, and pisiform) and a distal row of bones (trapezium, trapezoid, capitate, and hamate). Two sets of ligaments are also found: 1) an intrinsic or interosseous set of ligaments which connect the carpals directly, and 2) an extrinsic set of ligaments which are thickened portions of the wrist capsule. The wrist capsule is a firm fibrous layer surrounding the entire wrist, which has some areas of fibrous thickening which constitute the extrinsic dorsal and volar ligaments.

Acute injuries to the wrist ligaments may result from forward or backward falls onto an outstretched hand, as well as torsion or twisting injuries from outdoor sports and activities, and may be associated with fractures of the distal radius or carpal fractures. One of the most common injuries from such falls is a tear of the scapho-lunate ("S-L") ligament. Other ligaments, such as the Luno-Triquetral ligament can also tear and require repair.

BRIEF SUMMARY

Methods and kits are provided to treat scapho-lunate ligament tears, which involve stabilization of the scaphoid and lunate both dorsally and volarly. The treatments may be performed through open, mini-open or arthroscopic procedures, as an intra-capsular or extra-capsular repair and stabilization procedure. The treatment procedures may involve the use of sutures or wires to fix the relative orientations of the scaphoid and lunate, and the optional use of bone anchors or other bone attachment devices to create a capsulodesis between the lunate and scaphoid, or other bones, to lift the distal scaphoid into the desired position. Localization of the entry point of the sutures or wires into the bones using radio-opaque markers may be used to improve positioning of the bone anchors, sutures and wires.

A method of treating a patient, comprising making entry incision in a distal extremity of a patient, exposing a first bone and an adjacent second bone, drilling entry openings of first and second passageways in the first and second bones, respectively, radiographically confirming positioning of the dorsal openings, drilling the first and second passageways through the first and second bones to form exit openings, wherein the first and second passageways are oriented to permit fixation of the first and second bones, radiographically confirming positioning of the exit openings, looping a suture through the first and second passageways, and securing the suture to resist separation of the first and second bones. The method may further comprise drilling a third passageway in the second bone, wherein at least a portion of the third passageway is spaced farther from the articulation between the first and second bones than the second passageway, and optionally attaching a coupling member to the between the first bone and the third passageway of the second bone, and adjusting the coupling member to maintain fixation between the first and second bones. The method may also further comprise stabilizing the coupling member to adjacent non-bony tissue. The method may further comprise positioning radio-opaque markers at the dorsal openings of the first and second passageways, and may also include inserting tubular structures into the first and second passageways, wherein at least a portion of the tubular structures may or may not protrude from the exit openings of the first and second bones. Looping the suture may be performed using a tendon or suture retriever. The first and second passageways may each be angled about 30 to about 40 degrees away from the articulation of the first and second bones. In some variations, the entry incision is a dorsal wrist incision, and the drilling first and second passageways is performed in a volar direction, or at least one of the first and second passageways is angled away from an articulation of the first and second bones, or a ligament attached to the first and second bones. In some specific embodiments, the first and second bones are a scaphoid and a lunate, or alternatively a lunate and a triquetrum, or alternatively a scaphoid and a captitate. In some variations, at least one of the first and second bones is a carpal bone or a tarsal bone. The method may further comprise drilling a third passageway into the first bone, the third passageway spaced farther from the articulation between the first and second bones than the entry opening of the first passageway, and drilling a fourth passageway into the second bone. The third and fourth passageways may be coupled using a connector, and the tension in the connector may be manipulated to adjust the relative desired orientation between the first and second bones. The connector may also be attached to non-bony connective tissue using a capsulodesis material. Bone anchors may be inserted into the third and fourth passageways to facilitate coupling of the connector to the third and fourth passageways.

In another example, a method for treating a patient is provided, comprising making a dorsal wrist incision in a wrist region, the wrist region comprising an ulnar side, a radial side, a base of a palm, a carpal tunnel and a wrist crease, exposing the scaphoid and lunate, approximating the desired positions of the scaphoid and lunate, partially drilling a first passageway into a dorsal cortex of the scaphoid and a second passageway into a dorsal cortex of the lunate, each passageway comprising a dorsal opening, wherein the dorsal opening is spaced about 3 to 4 mm from a scapholunate ligament located between the scaphoid and lunate, placing guide wires into the first and second passageways, passing a tubular structures over the guide wires to the dorsal openings of the first and second passageways, radiographically confirming the positions of the tubular structures using radio-opaque markers, using a drill guide to complete drilling of the first and second passageways to form a volar openings at volar cortices of each of the scaphoid and lunate, wherein each of the first and second passageways form an angle of about 30 to 40 degrees from a perpendicular axis to the respective dorsal cortices of the scaphoid and lunate, away from the scapho-lunate ligament, making a volar wrist incision at the base of the palm, starting at a proximal extent of the carpal tunnel to a point 2 centimeters proximal to the wrist crease, the volar wrist incision comprising a zig zag incision across the ulnar side of the wrist region, exposing the volar wrist capsule to locate the tubular structures on volar surface scaphoid and lunate; passing a first retriever through one of the first or second passageways, inserting a retaining structure into the first retriever, the wire suture comprising a first end region and a second end region, pulling the retaining structure through the one of the first or second passageway using the first retriever, passing a second retriever through the other of the first or second passageways, inserting the retaining structure into the second retriever, pulling the retaining structure through the other of the first or second passageways using the second retriever, and connecting and securing first and second end segments of the retaining structure. The retaining structure may be a suture, cable or tape, and the suture may be a wire suture. The tubular structure may be a cannulated drill bit or cannulated peg. The method may further comprise drilling a third passageway into the scaphoid, the third passageway spaced farther from the S-L ligament than the dorsal opening of the first passageway, and drilling a fourth passageway into the lunate. The method may further comprise coupling the third and fourth passageways using a connector structure, and optionally adjusting the tension of the connector structure to achieve the desired relative orientation between the scaphoid and lunate. The method may further comprise securing the connector structure to a wrist capsule using a capsulodesis material. The connector structure may be coupled to the third and fourth passageways using bone anchors inserted into the third and fourth passageways. In some variations, the first retriever and the second retriever are the same retriever.

DETAILED DESCRIPTION

Figure 1:
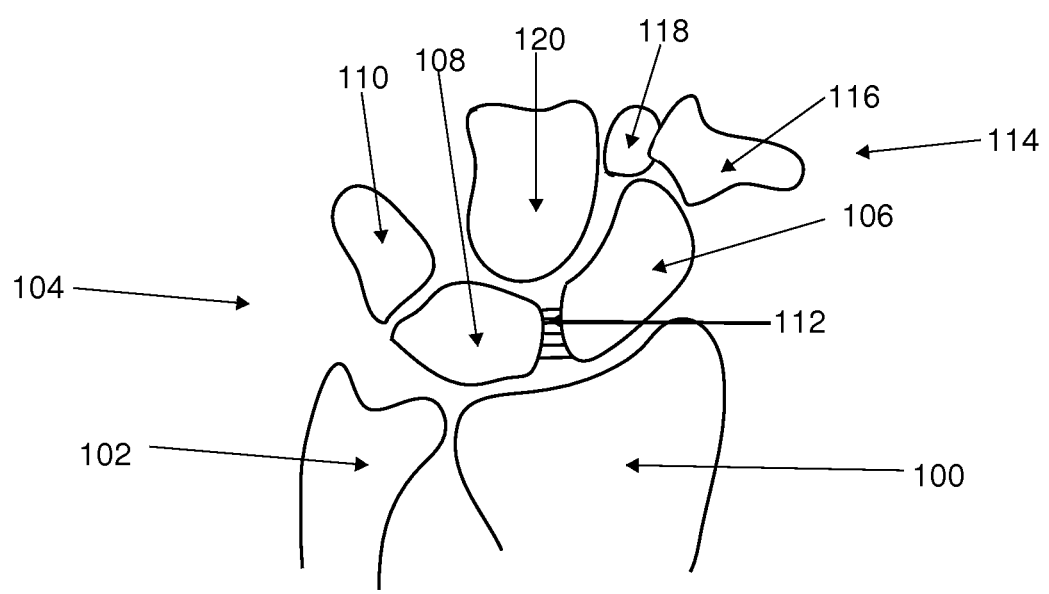
FIG. 1 is a schematic dorsal view of the wrist.

FIG. 1 is a schematic depiction of the bones comprising the wrist, which include the distal ends of the forearm bones, the radius 100 and ulna 102, that articulate with the proximal row 104 of carpal bones, the scaphoid 106, lunate 108 and triquetrum 110. Located between the scaphoid 106 and lunate 108 is the scapho-lunate ("S-L") ligament 112. The S-L ligament 112 comprises three regions, a strong dorsal segment with a strength of about 350 Newtons, a moderately strong volar segment with a strength of around 200 Newtons, and a weaker membranous region between the dorsal and volar segments. The proximal row 104 of carpal bones articulate with a distal row 114 of carpal bones, comprising the trapezium 116, trapezoid 118 and capitate 120 and hamate (not shown). Although the S-L ligament repair is described herein, the same procedure may be used to repair or stabilize other bones, such as the luno-triqueteal or scapho-capitate bones, or fractured parts of a broken bone such as a scaphoid bone. This allows fixation of the dorsal and volar or lateral and medial surfaces of bones to be connected and fixed. The repairs may be performed in carpal bones as well as between other bones, or between a carpal bone and another non-carpal bone.

The scaphoid is involved in the pathomechanics of wrist motion. Due to its attachment with the lunate via the S-L ligament, the scaphoid moves together with the lunate. For example, during wrist flexion, the lunate and scaphoid will flex together, and when the wrist is brought from ulnar to radial deviation, the scaphoid moves into a vertical position on lateral x-ray view, moving synchronously with the lunate. This unified movement provides smooth, painless wrist motion and normal functioning of the radio-carpal articulation.

On a normal posterior-anterior ("PA") x-ray film, the gap between the scaphoid and lunate is typically less than 3 mm, and on a lateral x-ray film, the scapholunate angle (i.e. the angle between lines bisecting the lunate and scaphoid) is in the range of about 30 to 60 degrees, or about 30 to 80 degrees. If the ligament between the scaphoid and lunate is torn or separated, on a PA film there may or may not be widening of the scapho-lunate gap, but on lateral film, the scaphoid flexes down, moving into a more volar position but also rotates to assume a more vertical appearance from a lateral view. The lunate, however, rotates dorsally instead of following the scaphoid. This is known as a Dorsal Intercalary Segment Instability pattern ("DISI"). In addition to causing an abnormal position and motion of the scaphoid at the radio-scapho joint, with time the instability may also cause the capitate to migrate distally, resulting in severe arthritis and collapse of the wrist. This results in a condition known as Scapho Lunate Advanced Collapse, or "SLAC "wrist.

There are considerable forces acting on the S-L ligament and failure to adequately repair it and correct the position and motion of the scaphoid may lead to the ultimate destruction of the wrist joint. However, because the S-L ligament is narrow and difficult, if not impossible, to directly repair, other methods are often employed to hold the scaphoid in a normal and horizontal position that aligns the scaphoid with the lunate and maintain the angle of 30 to 60 on the lateral view. There are two procedures that may be used to reduce and maintain a normal position between the scaphoid and the lunate so that the ligaments can heal.

The first procedure is a repair using whatever tissues are remaining of the S-L ligament, or use of other tissues to do so. While tendon grafts have been used before, tendon grafts tend not to hold up over time and have generally fallen out of favor. A variant procedure known as a bone-ligament-bone graft has also been advocated. This procedure involves taking a ligament graft from the foot that includes a small bone on each end of the donor ligament and then grafting the bone into the lunate and scaphoid and allow the bone to heal on both sides. This avoids repair of the ligament but has some technical difficulties and is not in general use.

The second type of procedure is a capsulodesis procedure, which reconstructs the dorsal extrinsic wrist capsule and ligaments by attaching the dorsal wrist capsule and the ligaments proximally to the distal region of the scaphoid, thereby suspending the scaphoid in a more horizontal position with the distal region of the scaphoid more dorsal. Such capsulodesis procedures have been used for many years but they have limited long term reliability. Variant of the capsulodesis procedure include the Blatt capsulodesis, which connects the capsule proximally to the radius, and the Brunelli procedure uses a complex method of suspending a tendon that is passed from volar to dorsal through the scaphoid to maintain the scaphoid in a horizontal orientation.

Other less common procedures involve stabilization of the S-L joint with the hope that the ligament will eventually heal. This can be done by simple pinning of the scaphoid and lunate, or placement of a screw along the rotational axis of the scaphoid. This screw has had technical problems is difficult to place and is not in common use.

Because of the poor outcomes of these procedures, many hand surgeons advocate more ablative procedures such as bone fusions as initial procedures. These ablative procedures may include scapho-capitate fusion, scapho-trapezium-trapezoid fusion or proximal row carpectomy.

It is hypothesized herein that one potential reason for the poor outcomes may be that the "repairs" of the S-L ligament are typically performed only on the dorsal surface, which may have a tendency to splay or "open" on the volar side due to asymmetric compressive forces being applied to the scaphoid and lunate. This asymmetry may actually result in volar-side instability post-repair.

In contrast, the repair procedures described herein involve passage of a suture/implant to both the dorsal and volar regions of the adjacent bones, which may position the bones in a more anatomic orientation to allow healing of both the dorsal and volar regions of the ligament. Both the interosseous ligament remnants and the extrinsic ligaments and capsule may be used for the "repair".

A capsulodesis may also be used between the lunate and the distal scaphoid to maintain the relationship of these two bones to each other using the extrinsic ligaments.

The procedure may be performed in an intra-capsular or extra-capsular fashion through a dorsal approach, and may be done arthroscopically on the dorsal side combined with a volar open approach through the carpal tunnel.

The patient may be prepped and draped in the usual sterile fashion. The procedure may be done under tourniquet control to reduce bleeding.

A dorsal wrist incision is made longitudinal or transverse centered at the S-L region and the scaphoid and lunate are exposed. Alternatively, the capsule can be left intact and the initial pins placed with a mini-incision of ½ to 2 or 3 cm.

An incision is made transversely or longitudinally into the dorsal wrist capsule, preserving the extrinsic ligament to be used for the S-L repair and for the capsulodesis. The S-L ligament can be directly visualized by this open method, or may be visualized by a preliminary arthroscopy.

Figure 2A:
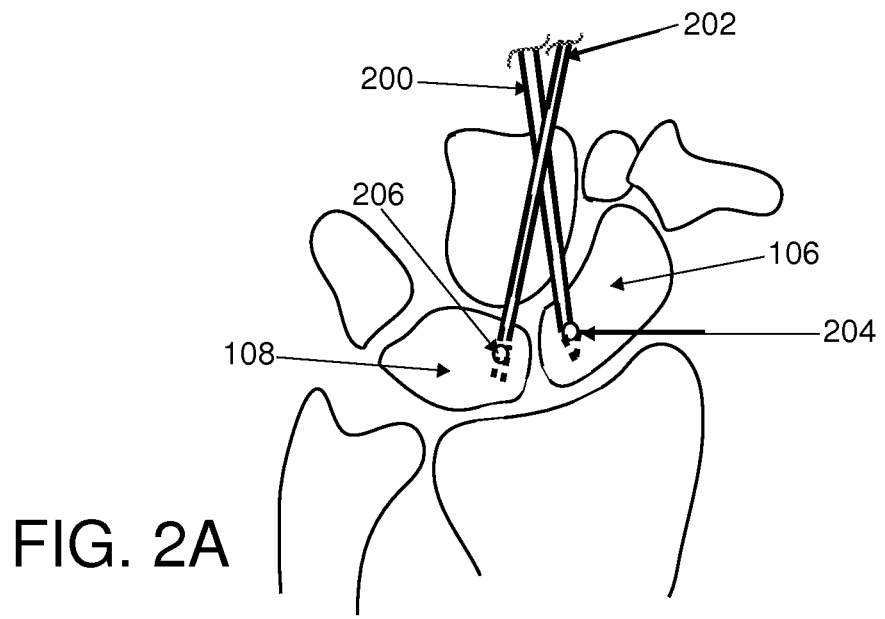
FIGS. 2A and 2B are schematic dorsal and lateral views of the wrist and the initial insertion of guide wires into the scaphoid and lunate.
Figure 2B:
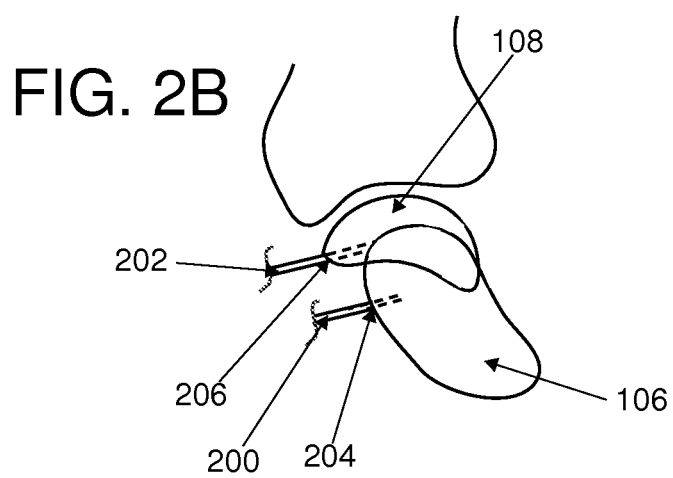

Referring to FIGS. 2A and 2B, to begin ligament approximation and bone positioning for the S-L ligament repair, a guide wire 200, 202 is placed in either the scaphoid 106 or lunate 108 and drilled or otherwise inserted a short distance into the bone. The guide wire 200, 202 is inserted into the dorsal cortical surface of the bone, which forms a dorsal opening 204, 206. Examples of such wires include any of a variety of Kirschner wires, commonly known as K-wires, which may be drilled by hand or machine, or even hammered into the bone. In some variations, the capsule is opened and the wire may be inserted intra-capsularly under direct vision. In other variations, the wire may be directly inserted extracapsularly, e.g. through the wrist capsulewithout initially opening the wrist capsule Referring to FIGS. 3A and 3B, a ball 300 or other radio-opaque object or marker may be attached to the wire 200, 202 or passed over the wire to the dorsal opening 204, 206 where the wire 200, 202 enters the bone. This ball 300, clip or object can be seen on X-ray and may provide more accurate location of where the wire 200, 202 enters the bone. The wire and marker placement is repeated for the other bone. In some variations, the dorsal opening should be about 3 to about 4 mm from the S-L ligament (not shown in FIG. 3) to provide secure and stable attachment of the wire to the bone. Plain film radiography may confirms the exact position of the K-wires 200, 202 entry point at the dorsal openings 204, 206 to confirm correct placement of the drill holes.

Figure 3A:
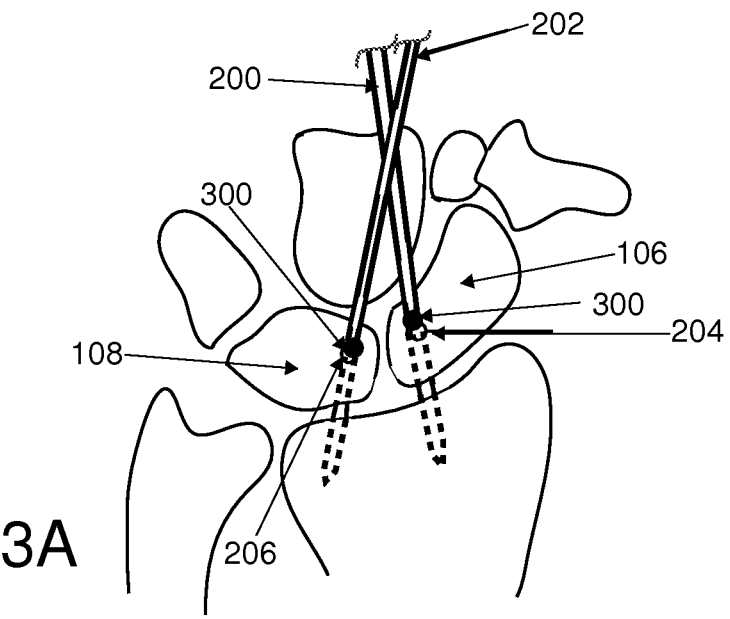
FIGS. 3A and 3B are schematic dorsal and lateral views of the wrist and the completed insertion of guide wires through the scaphoid and lunate and out of the volar surfaces.
Figure 3B:
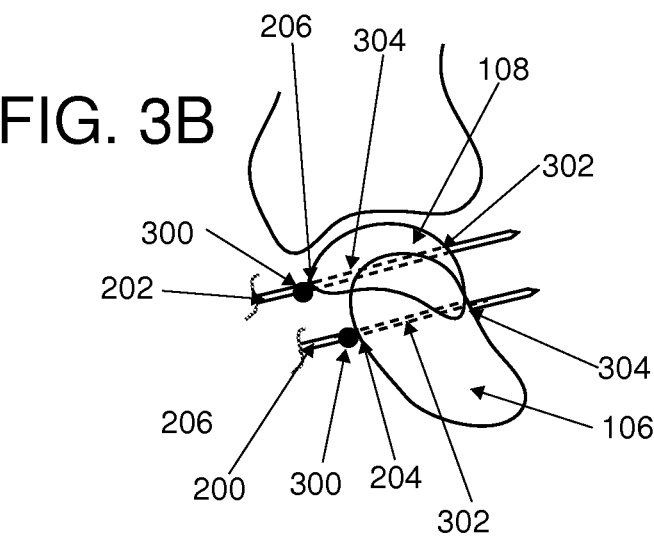

As depicted best in FIG. 3B, the wires 200, 202 are then drilled through to the volar cortex and out the volar side of the bones, forming passageways 302, 304 and volar openings 306, 308 in the scaphoid 106 and lunate 108, respectively. The K-wires 200, 202 may be used for drilling, or a cannulated drill bit over the K-wires 200, 202 or a larger bit may be used. In one embodiment, the wires may be blunt-tipped wires so as to reduce potential damage to nerves and/or tendons as the wires protrude from the volar surfaces of the bone. The wire may be used to insert a cannulated peg, a cannulated drill bit or other cannulated structure (e.g. a hollow plastic tube). During the procedure, the wires and cannulated structures may be replaced with solid polymer or metal pegs. The pegs may comprise an atraumatic tip a soft material to reduce inadvertent tissue damage. As shown in FIG. 3A, the wires 200, 202 are drilled at an angle of approximately 30 to 40 degrees from the dorsal cortex of the scaphoid 106 and lunate 108 in the volar direction away from the S-L ligament or articulation between the scaphoid 106 and lunate 108. In some variations, the wires 200, 202 may be positioned to be close to the articular surfaces of the bones, or to otherwise reduce or minimize the disruption of the articular surfaces of the scaphoid and lunate.

In some variations, a drill guide with one fixed guide and a variable guide, or two variable guide, or two fixed guide, may be used to facilitate angled drilling of the passageways. The variable or fixed guide may be configured to be selectively or fixedly spaced from the other guide (fixed or variable guide) at a distance of about 3 mm, about 4 mm, about 5 mm, about 6 mm, or about 7 mm or more, and may be fixed or settable at an angle of about 10 degrees, about 20 degrees, about 30 degrees, about 40 degrees, about 50 degrees, or even about 60 degrees from the perpendicular axis to the dorsal cortical surface. In some further variations, the drill guide may have depth markings at about 2 mm, about 2.5 mm, or about 3 mm and/or a stop structure that may be set to limit excess depth of drilling. The drill bit may be solid or cannulated, and if cannulated may be preferably have an internal diameter size to accommodate the suture/wire/cable/tape. Typically, but not always, the diameter may be in the range of about 2 mm to about 3 mm.

Next, a volar wrist incision may be formed at the base of the palm, typically at the proximal extent of the carpal tunnel and advanced proximally to a point about 2 cm proximal to the wrist crease. A zig zag incision across the ulnar side to the wrist is generally ideal. A dissection is then performed between the ulnar neurovascular bundle and the finger forearm muscles, such as the flexor digitorum profundus, and into onto the wrist joint capsule. The wrist joint capsule is then exposed on the volar side. A radial incision on the radial side of the finger flexors may also be used to expose the volar wrist joint capsule.

Figure 4:
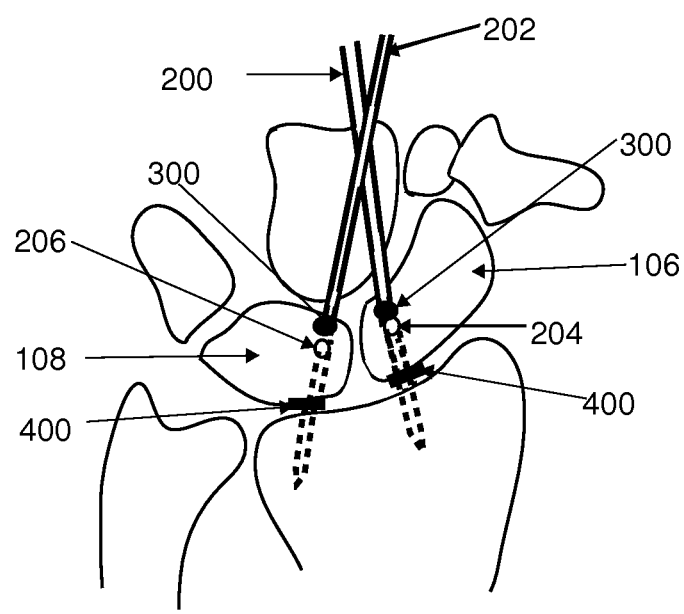
FIG. 4 is a schematic dorsal view of the wrist with radio-opaque markers and pegs located at the dorsal and volar openings of the attachment pathways, respectively.

Referring to FIG. 4, after the passageways 302, 304 and volar openings 306, 308 are made in the scaphoid 106 and lunate 108, additional radio-opaque markers 400 may be coupled to the wire about the volar openings 306, 308 to facilitate identification of the volar openings 306, 308. In some further variations, the dorsal and volar radio-opaque markers 300, 400 have different shapes and/or sizes visible on plain film or fluoroscopy, but in other variations, the dorsal and volar radio-opaque markers 300, 400 may have a similar shape or size. With radio-opaque markers 300, 400 positioned about the points of entry and exit of the wire into the bone, the desired positioning of entry and exit of the wire/peg may be confirmed radiographically.

Once correct positioning is confirmed, the markers 300, 400 may be removed and pegs may be inserted into the dorsal openings 204, 206 and through the passageways 302, 304 to partially exit or protrude from the volar openings 306, 308. The pegs may be hollow and cannulated, or may be removed and a tendon retriever or passer with a suture retriever on the end is passed through the passageway 302, 304 or through the cannulated peg onto the volar side. The tendon retriever may be a flexible nitinol or any other substance that would be capable of 'capturing' the sutures/implant for passage. The retriever may be passed from dorsal opening 204, 206 to respective volar opening 304, 306 through either passageway 302, 304, or through the cannulated peg or drill bit or plastic tube and/or may be passed the opposite direction.

The implant/suture may then be passed into or otherwise coupled to the tendon retriever, which is retrieved or withdrawn to thereby pass the implant/suture from the volar incision through the passageway 302, 304 of the bone and out of the dorsal opening 304, 306, where it may be clamped slightly away from the bone surface so as not to inadvertently decouple from the passageway 302, 304.

Figure 5:
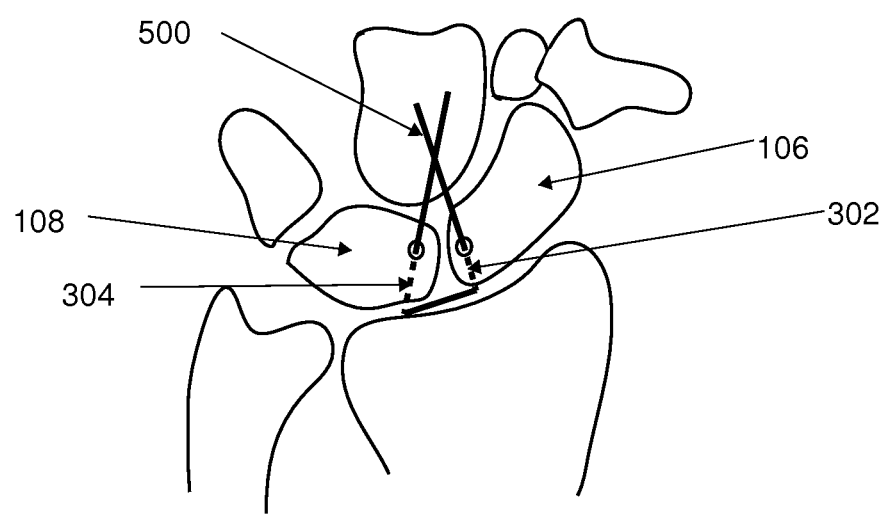
FIG. 5 is a schematic dorsal view of the wrist with a suture wire passed through the attachment pathways of the scaphoid and lunate.

As shown in FIG. 5, the other side of the suture/implant 500 is then passed through the passageway 302, 304 of the other bone to create a loop from dorsal surface around the volar side and back onto the dorsal side of the wrist. In some examples, a single loop may be used, but in other variations, multiple loops, or other loop patterns, or combinations thereof may be used, including "figure of eight" or "figure of six" loops. In still other variations, more than two passageways may be formed in the bones to permit use of additional patterns of wire fixation Any of a variety of suture(s), cable(s), tape(s) or otherelongate implant(s) may be used, including but not limited to monofilament steel or other metal, multi-filament steel or other metal, a mono-filament or multi-filament polymeric material, or a combination of metal and polymeric materials. In some variations, the suture/elongate implant may comprise a ribbon or tape-like structure. The polymeric materials may comprise a resorbable or non-resorbable polymeric material. The multi-filament sutures or elongate implants may be woven or non-woven. The suture/elongate implant may also be infused, embedded, or coated with any of a variety of drug-eluting materials and/or therapeutic agents, or tissue-ingrowth materials. A variety of the characteristics are contemplated to be mixed and matched to achieve the desired set of properties.

The repair on the dorsal side may be done outside the capsule, e.g. using a needle, the suture may be brought through the capsule and the suture/implant is fixed or connected outside the capsule. Alternatively, the dorsal side repair may be performed from inside the capsule on the surface of the scaphoid and lunate bones.

Sutures, joysticks or other temporarily attachable manipulation devices of any size may be attached to any or all of the bones to facilitate positions the bones for fixation in the desired anatomic positions or orientations.

Figure 6A:
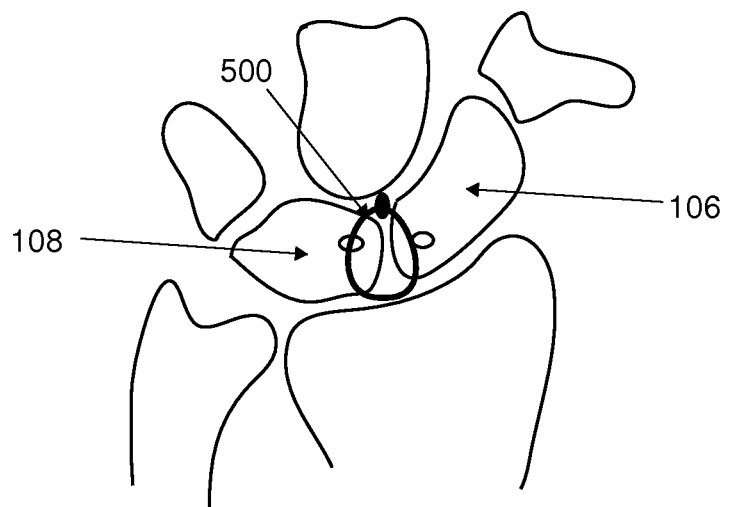
FIGS. 6A and 6B are schematic dorsal and lateral views of the wrist with the suture wire cinched and closed.
Figure 6B:
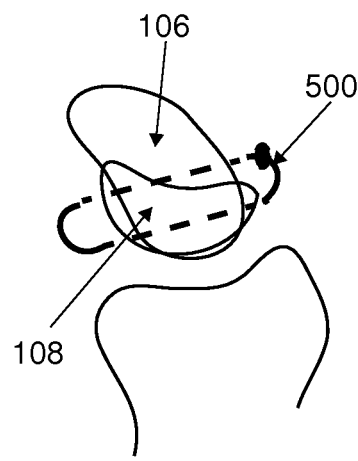

Referring now to FIGS. 6A and 6B, the two end regions of the suture/implant 500 may be connected by any of a variety of procedures or devices, e.g. with suture/implant 500 comprising metal wires, the end regions may be a twisting together, or otherwise tied together. In other variations, a crimping device, a cinching device with a resistance fit, or other securing device may be attached to the suture/implant 500 to secure the desired tension in the suture/implant 500 and maintain the position between scaphoid 106 and lunate 108. In still other variations, the end regions of the suture/implant 500 may be glued, soldered and/or welded together. In other variations, the suture/implant may be coupled on the volar side of the repair, rather than the dorsal side, or on both sides of the repair.

Optionally, a capsulodesis may be performed to further fixate the scaphoid 106 and lunate 108 (or other two bones of the wrist). The capsulodesis may be performed using bone anchors and/or extrinsic ligaments with capsule, and with or without the use of additional materials such as an allograft tendon or ligament suture. If used, any of a variety of ligament suture may be used, including ligament tape sutures.

Figure 7:
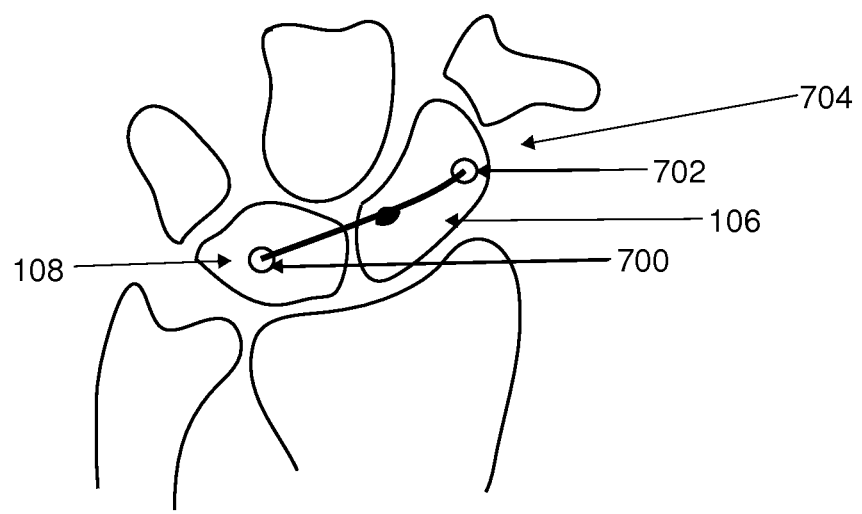
FIG. 7 is a schematic dorsal view depicting the use of bone anchors in a capsulodesis involving the scaphoid and lunate.

Referring to FIG. 7, one point of attachment 700 is at the lunate 108 and a second point of attachment 702 may be at the scaphoid 106 at any point the gives the best mechanical advantage to bring the scaphoid into a horizontal position and maintain a normal position relative to the lunate. This is generally, but not always, in the distal third 704 of the scaphoid 106.

A first wire may be drilled into the lunate and a second wire may be drilled into the scaphoid, again either by opening and exposing the bones or by drilling through the capsule and in either case the same method of exactly locating the point of entry of the wire into the bone is confirmed by using the cannulated ball or some other radio opaque object attached to the wire at the point of entry into the bone, as described above.

In this exemplary embodiment, the additional passageways are formed in the bones to perform the capsulodesis, but in other embodiments, one or more of the passageways used for the suture/implant 500 may also be used for the capsulodesis. Likewise, although the capsulodesis passageways may be formed in a similar fashion as the passageways 302, 304 for the suture/implant 500, in a dorsal to volar direction, in other variations, one or more of the capsulodesis passageways may be formed from a volar to dorsal direction, or any of the other variations described herein.

The anchor or attachment is connected to the bone by attachment of a bone anchor to the points of attachment 700, 702 or to passageways in the bones using a suture on the far side of the bone to secure the suture to the bone. A strip of ligament or capsule or allograft or tendon or other substance may be passed under the suture or tape to hold the ligament, capsule, allograft, tendon or other substance or material to secure the suture to the capsule until healing has occurred.

If the two or more anchors are placed, the capsulodesis material, e.g. the ligament, capsule, capsule allograft, tape, and the metal or polymeric suture (monofilament or multifilament or other structure) may be pulled taught to bring the scaphoid into the correct angle with the lunate, and then fixed or otherwise securably maintained by tying a knot, crimping or twisting the suture 706, as schematically depicted in FIG. 7.

The rest of the capsule may then be closed and the wrist may be immobilized for a period of time to facilitate healing. Physical therapy may be initiated during or after wrist immobilization.

Although various exemplary embodiments are described herein, additional embodiments and alterations to the described embodiments are contemplated within the scope of the disclosure. Thus, no part of the foregoing description should be interpreted to limit the scope of the invention as set forth in the following claims. For all of the embodiments described above, the steps of the methods need not be performed sequentially.

What is claimed is:

1. A method for repairing a damaged scapho-lunate ligament of a scapho-lunate bones of a patient, comprising:
   making a dorsal wrist incision in a wrist region, the wrist region comprising an ulnar side, a radial side, a base of a palm, a carpal tunnel and a wrist crease;
   exposing the scaphoid and lunate bones;
   reducing the scaphoid and lunate bones into positions approximating a normal anatomical alignment of the scaphoid bone and lunate bone;
   partially drilling a first passageway into a dorsal cortex of the scaphoid bone and a second passageway into a dorsal cortex of the lunate bone, each passageway comprising a dorsal opening, wherein the dorsal opening is spaced about 3 to 4 mm from the scapho-lunate ligament located between the scaphoid bone and lunate bone;
   placing guide wires into the dorsal openings of the first and second passageways extending in the scaphoid and lunate bones;
   passing tubular structures over the guide wires to the dorsal openings of the first and second passageways extending in the scaphoid and lunate bones;
   using a drill guide to complete drilling of the first and second passageways through the scaphoid and lunate bones to form a volar opening at volar cortex of each of the scaphoid bone and lunate bone, wherein each of the first and second passageways form an angle of about 30 to 40 degrees from a perpendicular axis to the respective dorsal cortices of the scaphoid bone and lunate bone, away from the scapho-lunate ligament;
   making a volar wrist incision at the base of the palm, starting at a proximal extent of the carpal tunnel to a point 2 centimeters proximal to the wrist crease;
   exposing the volar wrist capsule to locate the tubular structures on volar surface of the scaphoid bone and lunate bone;
   passing a first suture retriever through one of the first or second passageways;
   inserting a first end region of a retaining structure into the first suture retriever;
   pulling the retaining structure through the one of the first or second passageway using the first suture retriever;
   passing a second suture retriever through the other of the first or second passageways;
   inserting a second end of the retaining structure into the second suture retriever;
   pulling the retaining structure through the other of the first or second passageways using the second suture retriever; and
   connecting and securing the first and the second end regions of the retaining structure to each other to resist separation of the retaining structure from the scaphoid bone and lunate bone and to maintain the normal anatomical alignment of the scaphoid bone and lunate bone.

2. The method of claim 1, wherein the retaining structure is a suture, tape or multifilament stainless steel cable.

3. The method of claim 2, wherein the retaining structure is a multifilament stainless steel cable.

4. The method of claim 1, wherein the tubular structure is a cannulated drill bit, solid polymer, plastic, metal or cannulated peg.

5. The method of claim 1, further comprising:
   drilling a third passageway into the scaphoid, the third passageway spaced farther from the scapho-lunate ligament than the dorsal opening of the first passageway; and
   drilling a fourth passageway into the lunate.

6. The method of claim 5, further comprising coupling the third and fourth passageways using a retaining structure.

7. The method of claim 6, further comprising adjusting the tension of the retaining structure to achieve the desired relative orientation between the scaphoid and lunate.

8. The method of claim 6, wherein the retaining structure is coupled to the third and fourth passageways using bone anchors inserted into the third and fourth passageways.

* * * * *